(12) United States Patent
Patnaik et al.

(10) Patent No.: US 9,211,098 B2
(45) Date of Patent: Dec. 15, 2015

(54) ANATOMICAL SUPPORT FACILITATING MEDICAL IMAGING OF THE HIP, LEG AND KNEE

(71) Applicant: University of Cape Town, Cape Town (ZA)

(72) Inventors: Sarthak Patnaik, Keonjhar (IN); Sudesh Sivarasu, Cape Town (ZA)

(73) Assignee: University of Cape Town, Cape Town (ZA)

( * ) Notice: Subject to any disclaimer, the term of this patent is extended or adjusted under 35 U.S.C. 154(b) by 0 days.

(21) Appl. No.: 14/534,277

(22) Filed: Nov. 6, 2014

(65) Prior Publication Data

US 2015/0124942 A1 May 7, 2015

(51) Int. Cl.
| | | |
|---|---|---|
| A61G 7/075 | (2006.01) | |
| A61B 6/04 | (2006.01) | |
| A61B 5/00 | (2006.01) | |
| A61B 6/00 | (2006.01) | |

(52) U.S. Cl.
CPC .............. *A61B 6/04* (2013.01); *A61B 5/4571* (2013.01); *A61B 5/4585* (2013.01); *A61B 6/505* (2013.01)

(58) Field of Classification Search
CPC ...................................................... A61G 7/075
USPC ...................................... 5/621–624, 648–654
See application file for complete search history.

(56) References Cited

U.S. PATENT DOCUMENTS

| | | | |
|---|---|---|---|
| 2,581,110 A | | 1/1952 | Kenworthy |
| 4,027,869 A | * | 6/1977 | Ruiz ................................. 5/601 |
| 4,103,170 A | * | 7/1978 | Spradlin ....................... 378/179 |
| 4,403,357 A | | 9/1983 | Degen |
| 2012/0318278 A1 | | 12/2012 | Aboujaoude et al. |

FOREIGN PATENT DOCUMENTS

| | | |
|---|---|---|
| DE | 3609535 | 9/1987 |
| FR | 2576510 | 8/1986 |
| FR | 2580488 | 10/1986 |
| WO | WO 99/23991 | 5/1999 |

* cited by examiner

*Primary Examiner* — Fredrick Conley
(74) *Attorney, Agent, or Firm* — Remenick PLLC

(57) ABSTRACT

An anatomical support is provided for facilitating the medical imaging of a patient's hip, leg or knee. The anatomical support has an operatively horizontal pelvis support panel to one edge of which is attached an edge of a thigh locating panel by a hinged attachment and that has attached to an opposite edge thereof by another hinged attachment, a calf or foot support panel. The pelvis support panel has anchorage attachments for a pelvis restraint, and the thigh locating panel has anchorage attachments for a thigh restraint. Locking means are provided for locking the calf or foot support panel in adjustable positions in which it is generally parallel to the pelvis support panel but horizontally displaced therefrom. At least appropriate areas of the calf or foot support panel, the thigh locating panel and the pelvis support panel are made of radiolucent material.

6 Claims, 4 Drawing Sheets

ANATOMICAL SUPPORT FACILITATING MEDICAL IMAGING OF THE HIP, LEG AND KNEE

REFERENCE TO RELATED APPLICATIONS

This application claims priority to UK Application No. 1319689.4 filed Nov. 7, 2013, the entirety of which is hereby incorporated by reference.

FIELD OF THE INVENTION

This invention relates to an anatomical support for facilitating the medical examination and imaging of the hip, leg and knee of a patient in order to assess any injury that may have occurred; any deformity that may exist; or the success or otherwise of any surgery that has been performed on the leg.

Most importantly, but not exclusively, the invention is concerned with the anatomical support of a patient's body in a manner that allows medical examination and imaging of the knee to be carried out in a variety of different degrees of flexion. The medical imaging, whilst it could be of any appropriate technological nature, is most commonly X-ray examination of one form or another.

BACKGROUND TO THE INVENTION

Stress radiographs have been used for several years to detect the amount of varus/valgus knee laxity in the knee joint. The popularity of radio graphic methods of monitoring the knee joint has, however, been adversely affected by the X-ray exposure of an assistant that performs the stress imaging. They are also used to evaluate the degree of compartmental involvement in degenerative osteoarthritis. The cruciate ligaments are thought to be a secondary stabilization mechanism in the varus/valgus orientation.

Stress X-rays are an essential component of the assessment of a patient with a knee ligament injury. Such X-rays provide an objective measure for determining the extent of an injury prior to surgery; assessing whether a partial ligament tear is healing non-operatively; and in assessing postoperative outcomes. The use of stress X-rays is also necessary to properly diagnose osteoarthritis and most multi-ligament knee injuries. A correct interpretation of acute and chronic ligament injuries or flexion in different angles of the knee is most valuable and many advances have been made in treatment protocols.

Total knee arthroplasty (TKA) has become a common procedure worldwide and each year numerous patients undergo the procedure with differing degrees of success. Similarly, in various arthroscopic cases there is a necessity for a stress view to determine the laxity of the knee joint. One of the prerequisites for a well-functioning total knee arthroplasty is its proper alignment and stability. Proper alignment is considered as a restoration of the anatomical axis of the femur of between 2.4 and 7.2 degrees of valgus. A body mass index of >41 $kg/m^2$ signifies the risk of failure of a total knee arthroplasty. A recent study showed that a deviation of 1° varus from neutral alignment increases the medial load share by 5%.

Instability is a well-recognized cause of poor functional outcome after total knee arthroplasty. The causes of instability after total knee arthroplasty include inadequate soft tissue balancing; loss of ligamentous integrity; component wear; improper component sizing; and component mal-positioning.

The popularity of radiographic methods of monitoring the knee joint has been adversely affected due to X-ray exposure of the radiographers/health assistants involved; the variability of the stress forces applied; the cost of the equipment; and the size and bulkiness of the equipment.

A standardized protocol for the flexion of a knee requires the knee to be set at various angles from full extension to 120° knee flexion. At times a lateral view X-ray needs to be taken to check whether a particular flexion angle at the instrument is equal to the actual flexion of the femur and tibia.

Initially in various studies, various Varus/Valgus laxity of the knee were measured at extension (0-20° flexion) and 75° flexion. Laxity at extension was measured using a TELOS™ arthrometer while the patient lay in a prone position.

The TELOS™ arthrometer is a device in which a pair of parallel bars supports a central pressure unit and two generally parallel arms extend away from the bars in the same direction. The one arm can receive a foothold whilst the other arm can receive a roller and the pressure unit can exert pressure on a pad between those two items. The arrangement is rather awkward and requires, in some instances, that the patient be orientated in a highly non-ergonomic position. Also there is no possibility of developing any comparative information as regards the patient's other knee. Because of the rather awkward positioning of the patient and the device, a radiographer needs to be present when X-rays are taken.

It is the aim of this invention to provide an anatomical support to facilitate the medical imaging of the hip, leg and especially the knee in which disadvantages perceived of the existing equipment available are diminished at least to some extent.

SUMMARY OF THE INVENTION

In accordance with this invention there is provided an anatomical support for facilitating the medical imaging of a patient's hip, leg or knee, the anatomical support comprising an operatively horizontal pelvis support panel to one edge of which is attached an edge of a thigh locating panel by a hinged attachment and that has attached to an opposite edge thereof by another hinged attachment a calf or foot support panel, and wherein the pelvis support panel has anchorage attachments for cooperation in use with a pelvis restraint, and the thigh locating panel has anchorage attachments for cooperation in use with a thigh restraint; and wherein locking means are provided for locking the calf or foot support panel in adjustable positions in which it is generally parallel to the pelvis support panel but horizontally displaced therefrom, and wherein the calf or foot support panel, the thigh locating panel and the pelvis support panel are made substantially entirely of radiolucent material.

Further features of the invention provide for the calf or foot support panel, the thigh locating panel, and the pelvis support panel to be made substantially entirely of an acrylic plastic sheet material such as that sold under the trade name PERSPEX™; and for the thigh locating panel to have a pair of juxtaposed openings therein with optional individual closures for selectively and temporarily closing the openings and wherein the openings can be selectively used to receive a generally horizontal leg of a patient whilst the other leg is supported and located relative to the thigh locating panel and calf or foot support panel.

Still further features of the invention provide for the anchorage attachments to be apertures through the relevant panel that are conveniently in the form of elongate slots that can receive restraints in the form of straps passing therethrough; for a mechanism to be included for releasably fixing the calf or foot support panel in parallel relationship relative to the pelvis support panel; and for the thigh locating panel to be movable between a position in which it is generally coplanar with the pelvis support panel and a position in which it extends upwards at about 90° to the pelvis support panel with the pelvis support panel and calf or foot support panel extending, in plan view, in opposite directions.

In order that the invention may be more fully understood, one embodiment thereof will now be described with reference to the accompanying drawings.

DETAILED DESCRIPTION WITH REFERENCE TO THE DRAWINGS

Figure 1:
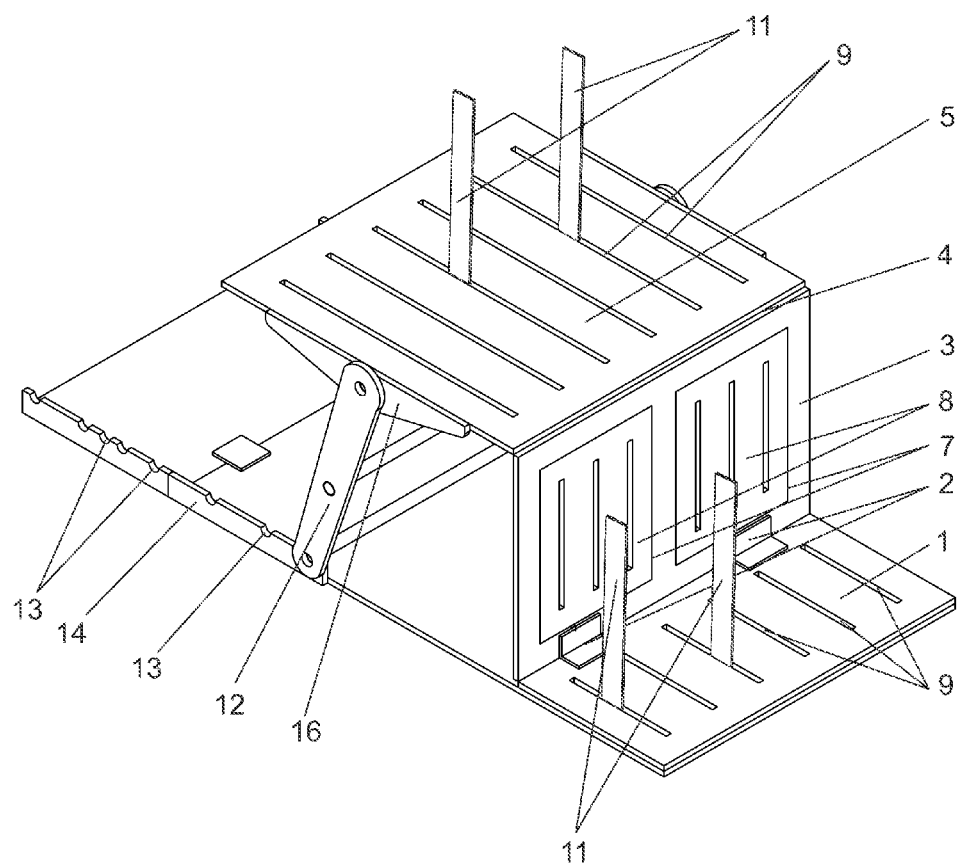
FIG. 1 is a schematic isometric view of one embodiment of the invention showing the calf or foot supporting panel in its uppermost elevation relative to the pelvis support panel.

In the embodiment of the invention illustrated in the drawings, an anatomical support for facilitating the medical imaging of a patient's hip, leg or knee comprises an operatively horizontal pelvis support panel (1) that can conveniently lie on the floor or on a somewhat elevated generally horizontal support structure such as an X-ray table. The panel can conveniently measure of the order of 600 to 800 mm square and conveniently about 700 mm square.

Attached to one edge of the pelvis support panel by way of suitable hinges (2) is one edge of a thigh locating panel (3). The thigh locating panel is rotatable between a generally horizontal position and a generally vertical position and can be fixed at any one of a number of predetermined inclinations that are selected according to a predetermined protocol that is selected for use. Such various positions are illustrated in FIGS. 4 to 7 of the accompanying drawings.

Attached to an opposite edge of the thigh locating panel by a hinged attachment (4) is a calf or foot support panel (5).

The arrangement is such that, when viewed in plan view, the calf or foot support panel extends in a direction opposite that in which the pelvis support panel extends so that in side view the panels assume the form of a squat open Zed.

The thigh locating panel has a pair of juxtaposed openings (7) therein with hinged closures (8) for selectively and temporarily closing each opening so that the openings can be selectively opened to receive a generally horizontal leg of a patient whilst the other leg is supported and located relative to the thigh locating panel and calf or foot support panel.

Each of the calf or foot support panel, the thigh locating panel and the pelvis support panel has anchorage attachments in the form of a series of parallel elongate slots (9) that can receive restraints in the form of straps (11) passing through them.

Figure 2:
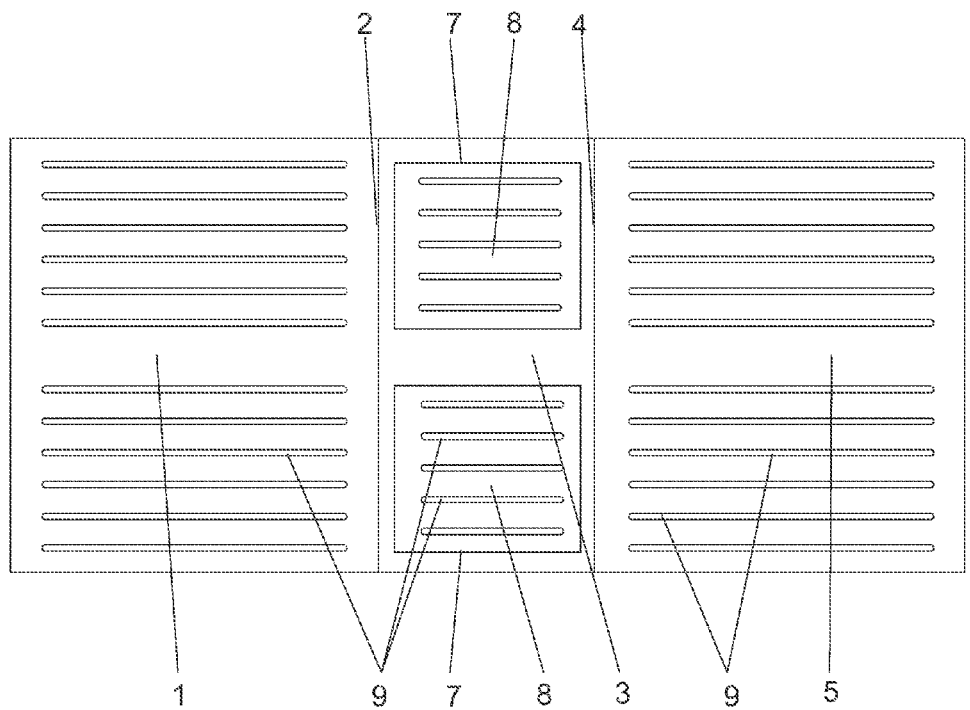
FIG. 2 is a schematic plan view of the anatomical support of the same embodiment of the invention in a collapsed flat condition.
Figure 3:
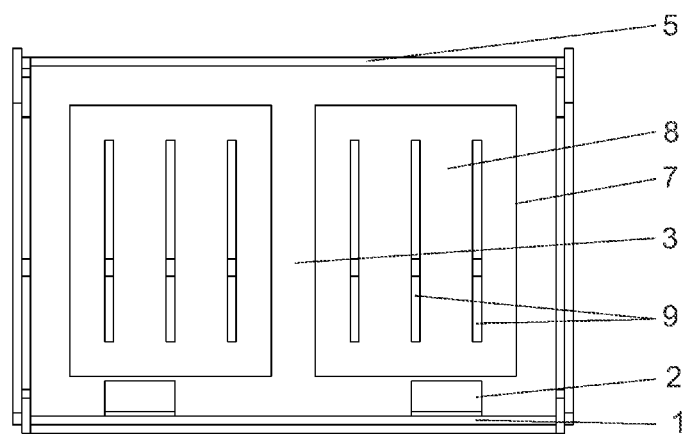
FIG. 3 is a schematic elevation of the embodiment of the invention in the position illustrated in FIG. 1 showing the thigh locating panel with a pair of juxtaposed openings therein with associated closures for selectively and temporarily closing the openings.
Figure 4:
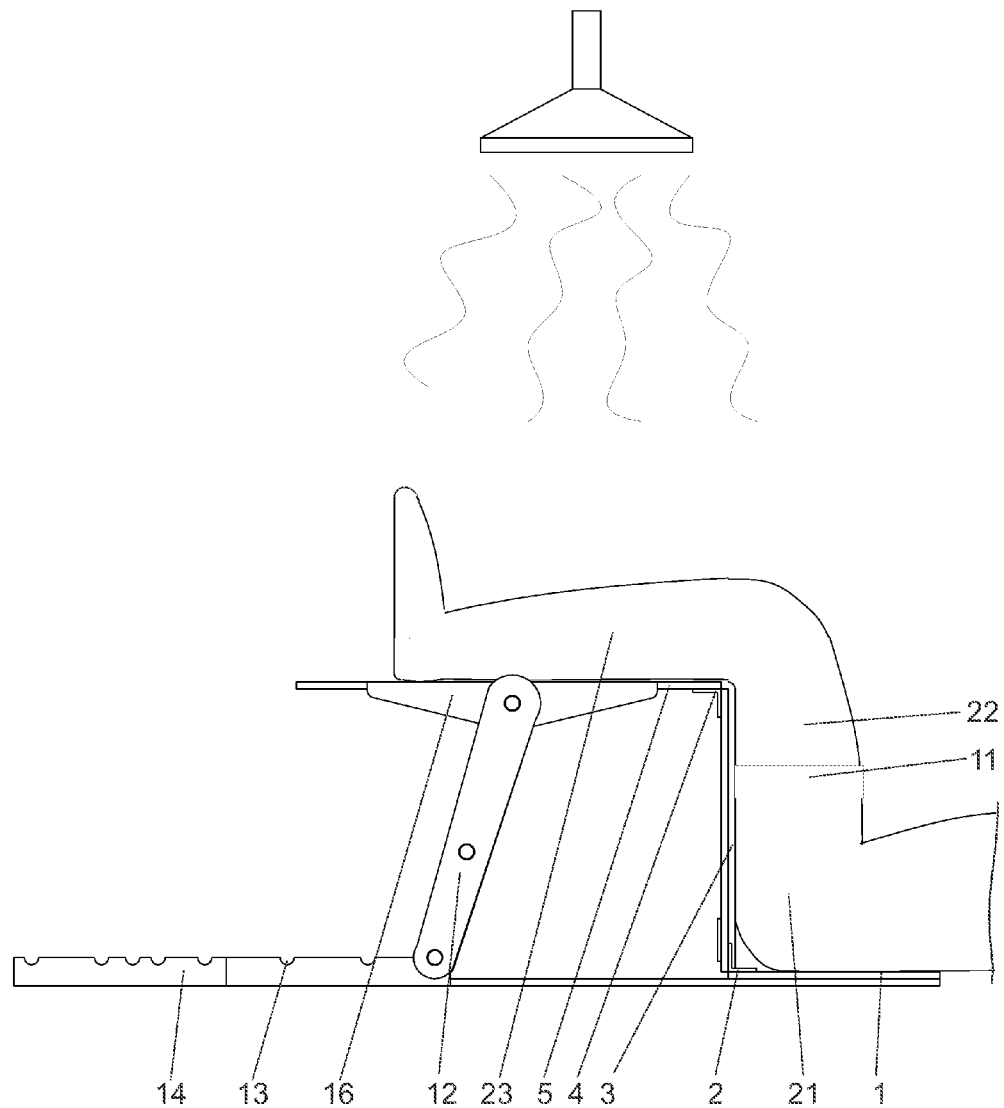
FIG. 4 is a schematic side view of the anatomical support illustrating its use with the calf or foot supporting panel in an upper elevation relative to the pelvis supporting panel.
Figure 5:
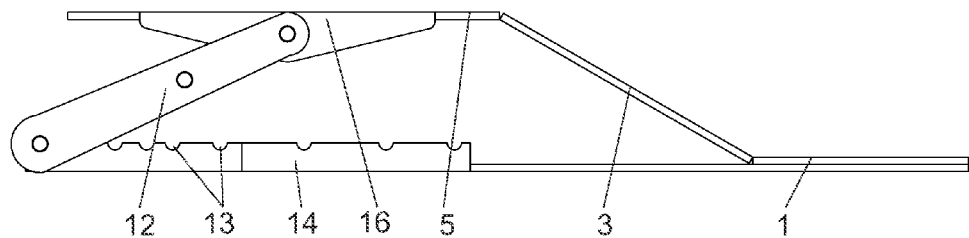
FIG. 5 is a schematic side view of the same embodiment of the invention showing the calf or foot supporting panel in a rather low elevated position relative to the pelvis supporting panel.
Figure 6:
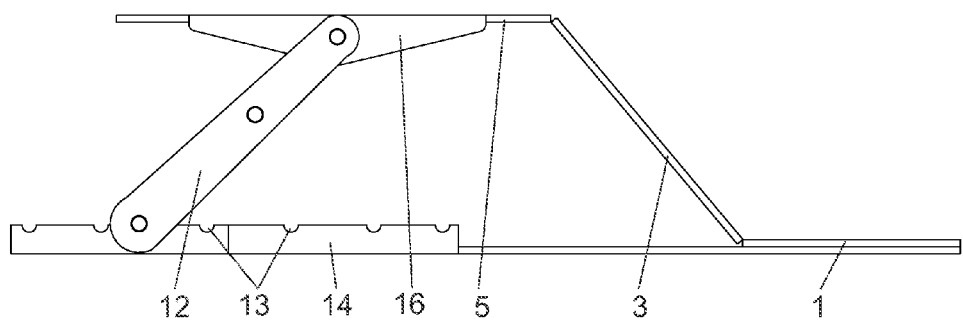
FIG. 6 is a schematic side view of the same embodiment of the invention showing the calf or foot supporting panel in an intermediate elevated position relative to the pelvis supporting panel.
Figure 7:
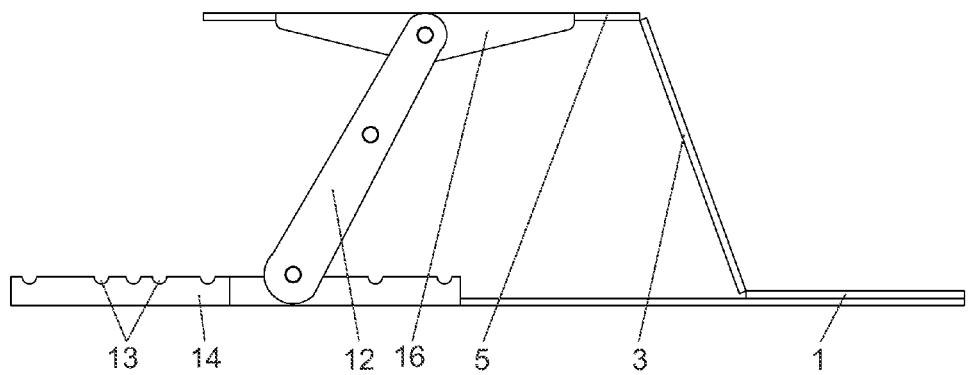
FIG. 7 is a schematic side view of the same embodiment of the invention showing the calf or foot supporting panel in an almost highest position relative to the pelvis supporting panel.

A mechanism is included for temporarily fixing the calf or foot support panel in parallel relationship relative to the pelvis support panel in selected adjustable positions in which it is generally parallel to the pelvis support panel but horizontally displaced therefrom. Such a mechanism can assume many different forms and, in this particular embodiment of the invention, includes a pair of parallel stays (12) whereof one is located at each side of the anatomical support and wherein the lower end can be engaged in a selected notch (13) in a frame member (14) so that each notch corresponds to a predetermined elevation of the calf or foot support panel relative to the pelvis support panel. In each of these positions, it will be quite apparent that the thigh locating panel assumes different inclinations to the horizontal as will be quite apparent from a reference to FIGS. 1 to 3 of the drawings. A locking plate (16) or other locking arrangement may be provided to maintain the thigh locating panel and the calf or foot support panel at the relevant inclination to each other.

As stated above, at least appropriate areas of the calf or foot support panel, the thigh locating panel and the pelvis support panel are made of radiolucent material. However, in this embodiment of the invention the calf or foot support panel, the thigh locating panel, and the pelvis support panel are all made substantially entirely of radiolucent material, especially a suitable thickness of acrylic plastic sheet material such as that sold under the trade name PERSPEX™.

In use, a patient is positioned on the anatomical support with the buttocks (21) on the pelvis support panel and the thighs (22) passing up the thigh locating panel with the calves (23) located on the calf and foot support panel. The inclination of the thigh locating panel can be set according to requirements and the object or objects to be achieved by radiography that is to be carried out. A leg that is not being subjected to examination can be passed through an opening (7) with the other leg supported as indicated. The raised knee can then be subjected to whatever imaging is required.

As may be required, the pelvis can be strapped to the pelvis support panel using the slots therein and, as may be required for the purposes of subjecting the knee under examination to lateral forces, the thigh can be strapped to the slots in the appropriate closure of the opening (7).

By suitably manipulating the anatomical support described above a large number of examinations can be carried out that were not heretofore possible and also, examinations can be carried out with the patient in a much more comfortable position than in the past.

The activities that can be conducted include developing a stress view of the knee joint in various flexion ranges and in full extension in a supine position. This is a much more user friendly situation than was possible in the past.

The anatomical support is thus versatile and multi-purpose with less occupational hazards to personnel who do not need to be present to ensure proper positioning of the patient when X-rays are taken. The anatomical support is therefore particularly suitable for use in the developing world.

The anatomical support can therefore be used to evaluate the valgus/varus stress around the knee joint; to determine the cartilage thickness, joint gap (medial and lateral); to evaluate the pre-operative and post-operative laxity in a knee joint post after a total knee arthroplasty; and to evaluate the flexion gap in various flexion ranges of movement.

Other uses include the estimation of the laxity in patients with medial collateral ligament and lateral collateral ligament injuries and the estimation of laxity in patients with anterior cruciate ligament and posterior cruciate ligament injuries.

It also enables an estimation of the patello femoral joint to be carried out as the knee can be flexed at 90°.

Imaging at various flexion angles provides details of joint structure congruency and indications on subluxation.

It is also planned to facilitate the measurement of the ankle ligament laxity as well as assessing a patient for hip arthroscopy by estimation of the hip joint space.

It also enables bilateral investigations to be carried out.

Numerous variations may be made to the embodiment of the invention described above without departing from the scope hereof.

Other embodiments and uses of the invention will be apparent to those skilled in the art from consideration of the specification and practice of the invention disclosed herein. All references cited herein, including all publications, and all U.S. and foreign patents and patent applications are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. An anatomical support for facilitating the medical imaging of a patient's hip, leg or knee, the anatomical support comprising an operatively horizontal pelvis support panel to one edge of which is attached an edge of a thigh locating panel by a hinged attachment and that has attached to an opposite edge thereof by another hinged attachment a calf or foot support panel, and wherein the pelvis support panel has anchorage attachments for cooperation in use with a pelvis restraint, and the thigh locating panel has anchorage attachments for cooperation in use with a thigh restraint; and wherein locking means are provided for locking the calf or foot support panel in adjustable positions in which it is generally parallel to the pelvis support panel but horizontally displaced therefrom, and wherein the calf or foot support panel, the thigh locating panel and the pelvis support panel are made substantially entirely of radiolucent material, in which the thigh locating panel has a pair of juxtaposed openings therein that can be selectively used to receive a generally horizontal leg of a patient whilst the other leg is supported and located relative to the thigh locating panel and calf or foot support panel.

2. An anatomical support as claimed in claim 1 in which the radiolucent material is an acrylic plastic sheet material.

3. An anatomical support as claimed in claim 1 in which the thigh locating panel is movable between a position in which it is generally coplanar with the pelvis support panel and a position in which it extends upwards at about 90° to the pelvis support panel with the pelvis support panel and calf or foot support panel extending, in plan view, in opposite directions.

4. An anatomical support as claimed in claim 1 in which the pair of juxtaposed openings have individual closures for selectively and temporarily closing the openings.

5. An anatomical support as claimed in claim 1 in which the anchorage attachments are apertures through the relevant panel.

6. An anatomical support as claimed in claim 5 in which the apertures are in the form of elongate slots that can receive restraints in the form of straps passing therethrough.

* * * * *